(12) United States Patent
Chaplin et al.

(10) Patent No.: US 9,040,500 B2
(45) Date of Patent: May 26, 2015

(54) METHOD FOR TREATING HEMATOPOIETIC NEOPLASMS

(75) Inventors: David Chaplin, Watlington (GB); Bronwyn G. Siim, Oxford (GB)

(73) Assignee: OXiGENE, Inc., South San Francisco, CA (US)

( * ) Notice: Subject to any disclaimer, the term of this patent is extended or adjusted under 35 U.S.C. 154(b) by 0 days.

(21) Appl. No.: 13/305,612

(22) Filed: Nov. 28, 2011

(65) Prior Publication Data
US 2012/0270831 A1    Oct. 25, 2012

Related U.S. Application Data

(63) Continuation of application No. 12/276,197, filed on Nov. 21, 2008, now abandoned.

(60) Provisional application No. 60/989,786, filed on Nov. 21, 2007.

(51) Int. Cl.

| | |
|---|---|
| A61K 31/70 | (2006.01) |
| A01N 43/04 | (2006.01) |
| A61K 31/66 | (2006.01) |
| A01N 57/00 | (2006.01) |
| A61K 31/661 | (2006.01) |
| A61K 31/52 | (2006.01) |
| A61K 31/675 | (2006.01) |
| A61K 31/7048 | (2006.01) |
| A61K 31/7068 | (2006.01) |

(52) U.S. Cl.
CPC .............. *A61K 31/661* (2013.01); *A61K 31/52* (2013.01); *A61K 31/675* (2013.01); *A61K 31/7048* (2013.01); *A61K 31/7068* (2013.01)

(58) Field of Classification Search
CPC .............. A61K 31/70; A61K 31/7068; A61K 31/7072; A61K 45/06
USPC .................................................. 514/49, 104
See application file for complete search history.

(56) References Cited

U.S. PATENT DOCUMENTS

| | | | |
|---|---|---|---|
| 4,940,726 A | 7/1990 | Pettit et al. | |
| 4,996,237 A | 2/1991 | Pettit et al. | |
| 5,409,953 A | 4/1995 | Pettit et al. | |
| 5,430,062 A | 7/1995 | Cushman et al. | |
| 5,525,632 A | 6/1996 | Obsumi et al. | |
| 5,561,122 A * | 10/1996 | Pettit ............................ 514/130 |
| 5,569,786 A | 10/1996 | Pettit et al. | |
| 5,674,906 A | 10/1997 | Hatanaka et al. | |
| 5,731,353 A | 3/1998 | Ohsumi et al. | |
| 6,150,407 A | 11/2000 | Tuse et al. | |
| 6,169,104 B1 | 1/2001 | Tuse et al. | |
| 6,201,001 B1 | 3/2001 | Wang et al. | |
| 6,423,753 B1 | 7/2002 | Dougherty | |
| 6,433,012 B1 | 8/2002 | Tuse et al. | |
| 6,538,038 B1 | 3/2003 | Pero et al. | |
| 6,593,374 B2 * | 7/2003 | Pinney et al. ............. 514/721 |
| 6,670,344 B2 | 12/2003 | Venit et al. | |
| 6,720,323 B2 | 4/2004 | Arnould | |
| 6,723,858 B2 | 4/2004 | D'Amato et al. | |
| 6,777,578 B2 | 8/2004 | Pettit et al. | |
| 6,787,672 B2 | 9/2004 | Potter et al. | |
| 6,794,384 B1 | 9/2004 | Potter et al. | |
| 6,846,192 B2 | 1/2005 | Tien | |
| 6,849,656 B1 | 2/2005 | Pinney et al. | |
| 6,855,702 B2 | 2/2005 | Venit et al. | |
| 6,919,324 B2 | 7/2005 | Chaplin et al. | |
| 6,992,106 B2 | 1/2006 | Morinaga et al. | |
| 7,018,987 B1 | 3/2006 | Pettit et al. | |
| 7,030,123 B2 | 4/2006 | Arnould et al. | |
| 7,037,906 B1 | 5/2006 | Lee | |
| 7,078,552 B2 | 7/2006 | Pettit et al. | |
| 7,087,627 B1 | 8/2006 | Davis | |
| 7,105,501 B2 | 9/2006 | Davis | |
| 7,105,695 B2 | 9/2006 | Pettit et al. | |
| 7,125,906 B2 | 10/2006 | Arnould | |
| 7,279,466 B2 | 10/2007 | Pettit et al. | |
| 7,358,236 B1 | 4/2008 | Chaplin et al. | |
| 8,198,302 B2 | 6/2012 | Chaplin et al. | |
| 2002/0035090 A1 * | 3/2002 | Zeldis et al. ............. 514/58 |
| 2002/0119951 A1 | 8/2002 | Seyedi et al. | |
| 2002/0183266 A1 * | 12/2002 | Bissery ............................ 514/34 |
| 2003/0109500 A1 | 6/2003 | Pero et al. | |
| 2003/0220298 A1 * | 11/2003 | Pettit et al. ............. 514/82 |

(Continued)

FOREIGN PATENT DOCUMENTS

| | | |
|---|---|---|
| EP | 0 276 051 | 7/1988 |
| WO | 92/16486 | 10/1992 |

(Continued)

OTHER PUBLICATIONS

Arditti et al. (Molecular Cancer Therapeutics (2005); 4(2) 325-331).*
ClinicalTrials.gov (2006).*
Hemapathology (2014).*
Arditti et al., "Apoptotic killing of B-chronic lymphocytic leukemia tumor cells by allicin generated in situ using a rituximab-alliinase conjugate." Mol. Cancer Ther., Feb. 2005, vol. 4, No. 2, pp. 325-331.
Bishop et al., "A randomized study of high-dose cytarabine in induction in acute myeloid leukemia." Blood, 1996, vol. 87, pp. 1710-1717.
Chaplin et al., "Anti-Vascular Approach to Solid Tumour Therapy: Evaluation of Combretastin A4 Phosphate." Anticancer Research, 1999, vol. 19, pp. 189-196.

(Continued)

*Primary Examiner* — Shirley V Gembeh
(74) *Attorney, Agent, or Firm* — Shay Glenn LLP (57) ABSTRACT

This invention relates to methods for treating a hematopoietic neoplasm comprising administering a therapeutically effective amount of a combretastatin compound, or a pharmaceutically acceptable salt thereof, to a subject having a hematological malignancy, wherein the combretastatin compound comprises a catechol or quinone moiety and is capable of forming a reactive oxygen species (ROS) in vivo. The method may further comprise co-administering a second chemotherapeutic agent.

11 Claims, 4 Drawing Sheets

(56) References Cited

U.S. PATENT DOCUMENTS

| | | |
|---|---|---|
| 2004/0024696 A1 | 2/2004 | Alves |
| 2006/0035868 A1 | 2/2006 | Chaplin et al. |
| 2007/0073077 A1 | 3/2007 | Pettit et al. |
| 2007/0149476 A1 | 6/2007 | Bissery |
| 2009/0192098 A1 | 7/2009 | Chaplin et al. |
| 2009/0264382 A1 | 10/2009 | Chaplin et al. |

FOREIGN PATENT DOCUMENTS

| | | |
|---|---|---|
| WO | 99/34788 | 7/1999 |
| WO | 99/35150 | 7/1999 |
| WO | 99/48495 | 9/1999 |
| WO | 00/06556 | 2/2000 |
| WO | 00/35865 | 6/2000 |
| WO | 00/48590 | 8/2000 |
| WO | 00/48606 | 8/2000 |
| WO | 00/73264 | 12/2000 |
| WO | 01/09103 | 2/2001 |
| WO | 01/12579 | 2/2001 |
| WO | 01/81288 | 11/2001 |
| WO | 01/81355 | 11/2001 |
| WO | 01/84929 | 11/2001 |
| WO | 02/14329 | 2/2002 |
| WO | WO02/22626 A1 | 3/2002 |
| WO | 02/50007 | 6/2002 |
| WO | 02/056692 | 7/2002 |
| WO | WO03/006743 A2 | 1/2003 |
| WO | 03/035008 | 5/2003 |
| WO | 03/040077 | 5/2003 |
| WO | 2004/078126 A2 | 9/2004 |
| WO | 2005/007635 | 1/2005 |
| WO | 2006/138427 | 12/2006 |

OTHER PUBLICATIONS

Combeau et al., "RPR112378 and RPR115781: Two Representatives of a New family of Microtubule Assembly Inhibitors." Molecular Pharmacology, 2000, vol. 57, pp. 553-563.

Dark et al., "Combretastatin A-4, an Agent That Displays Potent and Selective Toxicity toward Tumor Vasculature." Cancer Research, May 15, 1997, vol. 57, pp. 1829-1834.

Fang et al., "MZ3 induces apoptosis in human leukemia cells." Cancer Chemother. Pharmacol., 2007, vol. 59, pp. 397-405.

Folkes et al., "Oxidative Metabolism of Combretastatin A-1 Produces Quinone Intermediates with the Potential to Bind to Nucleophiles and to Enhance Oxidative Stress via Free Radicals." Chem. Res. Toxicol., 2007, vol. 20, pp. 1885-1894.

Hill et al., "Preclinical Evaluation of the Antitumour Activity of the Novel Vascular Targeting Agent Oxi 4503." Anticancer Research, 2002, vol. 22, pp. 1453-1458.

Holwell et al., "Combretastatin A-1 Phosphate a Novel Tubulin-binding Agent with In Vivo Anti Vascular Effects in Experimental Tumours." Anticancer Research, 2002, vol. 22, pp. 707-712.

Kaffy et al., "Synthesis and biological evaluation of vinylogous combretastatin A-4 derivatives." Org. Biomol. Chem., 2005, vol. 3, pp. 2657-2660.

Lin et al., "Functional activity of three distinct myeloperoxidase (MPO) promoters in human myeloid cells." Leukemia, 2002, vol. 16, pp. 1143-1153.

Madlambayan et al., "Leukemia regression by vascular disruption and antiangiogenic therapy." Blood, 2010, vol. 116, No. 9, pp. 1539-1547.

Nabha et al, "Effects of Combretastatin A-4 prodrug against a panel of malignant human B-lymphoid cell lines." Anticancer Drugs, 2000, vol. 11, pp. 385-392.

Nabha et al., "Evaluation of combretastatin A-4 prodrug in a non-Hodgkin's lymphoma xenograft model: preclinical efficacy." Anti-Cancer Drugs, 2001, vol. 12, pp. 57-63.

Nabha et al., "Combretastatin-A4 Prodrug Induces Mitotic Catastrophe in Chronic Lymphocytic Leukemia Cell Line Independent of Caspase Activation and Poly(ADP-ribose) Polymerase Cleavage." Clinical Cancer Research, Aug. 2002, vol. 8, pp. 2735-2741.

Petit et al., "The microtubule-targeting agent CA4P regresses leukemic xenografts by disrupting interaction with vascular cells and mitochondrial-dependent cell death." Blood, 2008, vol. 111, pp. 1951-1961.

Thomson et al., "Synthesis and biological properties of bioreductively targeted nitrothienyl prodrugs of combretastatin A-4." Mol. Cancer Ther., Nov. 2006, vol. 5, No. 11, pp. 2886-2894.

Wood et al., "Induction of apoptosis by anti-cancer drugs with disparate modes of action: kinetics of cell death and changes in c-myc expression." British Journal of Cancer, 1995, vol. 71, pp. 937-941.

Niazi et al. "Leukemic dermal infiltrates at permanent central venous catheter insertion site." (Abstract only) 1991.

Oh et al.; Expression of functional markers in acute lymphoblastic leukemia; Leukemia Research; 27; pp. 903-908; Oct. 2003.

* cited by examiner

METHOD FOR TREATING HEMATOPOIETIC NEOPLASMS

I. CROSS REFERENCE TO RELATED APPLICATIONS

This application claims the benefit of U.S. provisional patent application No. 60/989,786, filed 21 Nov. 2007.

II. INTRODUCTION

Cancer is a leading cause of death in the industrialized world and despite years of research, many types of cancer lack an effective therapeutic treatment. Although chemotherapy induces remission in the majority of adult patients with acute myeloid leukemia (AML), only a small percent are cured with conventional chemotherapy. Relapse of leukemias is in part due to the persistence of minimal residual leukemias that remain viable within specialized niches, such as vascular niches. Hence, novel treatment strategies are urgently needed to block the interaction of hematopoietic neoplasms with activated vascular cells, interfering with the establishment of pro-leukemic niches in various organs and to eradicate resistant disease.

Adhesion of leukemic cells to stromal cells has been shown to confer increased resistance to chemotherapeutic agents and diminish the rate of apoptosis of the leukemic cells. This process, named cell adhesion-mediated drug resistance (CAM-DR), depends on the interaction of integrins with their ligands. Adhesion of VLA4 (very late antigen 4, $\alpha4\beta1$) integrin-positive myeloid cells, to VCAM-1+ stromal cells is an important mediator of CAM-DR. Indeed, expression of VLA4 by leukemic cells portends a poor prognosis and a decreased five-year survival rate. Therefore, identification of novel anti-leukemic agents that inhibit interaction of leukemic cells with vascular cells provides novel strategies to target organ-infiltrating, angiogenesis-dependent leukemias.

Combretastatin A-1, a novel tubulin-destabilizing agent, was isolated from the South African tree *Combreturn caffrum*. Combretastatin A-1 binds to tubulin at the same site as colchicine, but with higher affinity. Its phosphate pro-drug, combretastatin A-1 phosphate (CA1dP) induces rapid microtubule depolymerization and vascular shutdown in subcutaneous solid tumors causing tumor necrosis at concentrations well below the maximum tolerated dose. Combretastatin A-1 comprises a single ortho-catechol moiety and is known to be capable of generating an enhanced antitumor response by forming reactive oxygen species (ROS) in the locality of the tumor in addition to selectively reducing the flow of blood to at least a portion of a tumor. This results in both direct inhibition of the proliferation of tumor cells, and tumor selective induction of hypoxia and subsequent necrosis in a portion of the tumor tissue without substantial necrosis of adjoining non-tumor tissue. Other catechol- and quinone-containing vascular disrupting agents have been shown to have enhanced therapeutic activity, relative to vascular disrupting agents that act solely through interaction with tubulin, particularly against sold tumors (see co-pending U.S. Ser. No. 10/790,662, U.S. Patent Publication No. 2004-024696, incorporated herein by reference in its entirety).

In this report, we show that combretastatin compounds that comprise a catechol or quinone moiety induce rapid cell death of non-adherent leukemic cells, at low, non-toxic doses. We also demonstrate that single-agent treatment with a catechol- or quinone-containing combretastatin compound is effective in eradicating both circulating, and vascular-adherent leukemic cells in subcutaneous mouse models of AML, without affecting normal hematopoiesis. CAldP-treated mice had significantly prolonged survival and significantly decreased tumor load. Co-administration of an additional chemotherapeutic agent, e.g. AraC, decreases tumor load even further. Therefore, catechol- or quinone-containing combretastatin compounds delivered alone or in combination with chemotherapeutic agents represent a promising novel therapeutic approach to eradicate hematopoietic neoplasms.

III. SUMMARY OF THE INVENTION

One aspect of the invention provides methods of treating a hematopoietic neoplasm comprising administering a therapeutically effective amount of a combretastatin compound, or a pharmaceutically acceptable salt thereof, to a subject having a hematological malignancy, wherein the combretastatin a quinone or catechol moiety and is capable of forming a reactive oxygen species (ROS) in vivo. Preferably, the combretastatin compound is an ortho-quinone, ortho-quinone prodrug, ortho-catechol or ortho-catechol prodrug. More preferably, the compound is combretastatin A1 (CA1) or combretastatin A-1 diphosphate (CA1dP), or a pharmaceutically acceptable salt thereof.

Another aspect of the invention provides the use of a combretastatin capable of forming a reactive oxygen species in vivo, particularly combretastatin A-1 or a prodrug and/or salt thereof, for the treatment of a hematopoietic neoplasm. The invention also contemplates use of a combretastatin capable of forming a reactive oxygen species in vivo in the preparation of a medicament for use in treating a hematopoietic neoplasm.

Yet another aspect of the invention provides methods of treating a non-solid tumor comprising administering, to a subject suffering from non-solid tumor, a therapeutically effective amount of combretastatin compound or a pharmaceutically acceptable salt thereof, wherein the combretastatin compound comprises a catechol or quinone moiety and is capable of forming a reactive oxygen species in vivo.

V. DETAILED DESCRIPTION

A. Definitions

As used herein, a "therapeutically effective amount" of combretastatin A-4 phosphate (CA4P), or a therapeutically acceptable salt thereof, according to the present invention is intended to mean that amount of the CA4P that will inhibit the growth of, or retard cancer, or kill malignant cells, and cause the regression and palliation of cancer, i.e., reduce the proliferation rate and/or the number of malignant cells within the body. Other desired anti-tumor effects include, without limitation, the modulation of neoplasm growth rates, the enhancement of necrosis or hypoxia in malignant cells, reduced retention of CEPs and other pro-angiogenic cells, amelioration or minimization of the clinical impairment or symptoms of hematopoietic neoplasms, extending the survival of the subject beyond that which would otherwise be expected in the absence of such treatment, and the prevention of neoplastic growth in an animal lacking any neoplasm formation prior to administration, i.e., prophylactic administration.

As used herein, the terms "modulate", "modulating" or "modulation" refer to changing the rate at which a particular process occurs, inhibiting a particular process, reversing a particular process, and/or preventing the initiation of a particular process. Accordingly, if the particular process is neoplastic growth or metastasis, the term "modulation" includes, without limitation, decreasing the rate at which neoplastic growth and/or metastasis occurs; inhibiting neoplastic growth and/or metastasis, including tumor re-growth following treatment with an anticancer agent; reversing neoplastic growth and/or metastasis (including tumor shrinkage and/or eradication) and/or preventing neoplastic growth and/or metastasis.

"Catechol" is any group of optionally substituted compounds with aryl functionality and containing at least two OH groups at ortho or para positions on the aryl ring, wherein a conjugated system is formed with at least one C=C bond. The preferred catechol of the present invention is an ortho-benzocatechol. The term "catechol" also encompasses catechols in prodrug form, wherein one or both hydroxyl groups are substituted with a moiety that is metabolically converted to hydroxyl in vivo.

"Quinone" is any group of optionally substituted aromatic polyketone compounds derived from a compound with an aryl moiety. At least two C=O groups are in the ortho or para position on the aryl ring, and form a conjugated system with at least one C=C bond. The preferred quinone of the present invention is an ortho-benzoquinone. Quinones can be synthesized in a number of ways by oxidation of a phenolic precursor such as ortho-catechol. The oxidant reagents used in the reaction can include Jones reagent (Chromate salts), Fremy's salt ($(KSO_3)_2NO$), and the like. Such oxidation also can occur in vivo by virtue of chemical or enzymatic activity. The preferred oxidant is o-iodoxybenzoic acid.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like.

"Aryl" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like), provided that the point of attachment is through an atom of the aromatic aryl group. Preferred aryl groups include phenyl and naphthyl.

"Halo" or "halogen" refers to fluoro, chloro, bromo, and iodo and is preferably fluoro or chloro.

"Hydroxy" or "hydroxyl" refers to the group —OH.

As used herein, the term "prodruq" refers to a precursor form of the drug which is metabolically converted in vivo to produce the active drug. Thus, for example, combretastatin phosphate prodrug salts administered to an animal in accordance with the present invention undergo metabolic activation and regenerate combretastatin A-1 in vivo, e.g., following dissociation and exposure to endogenous non-specific phosphatases in the body, the drug which is metabolically converted in vivo to produce the active drug. Preferred prodrugs of the present invention include the phosphate, phosphoramidate, or amino acid acyl groups as defined herein. The phosphate ester salt moiety may also include (—OP(O)(O-alkyl)$_2$ or (—OP(O)(O$^-$NH$_4^+$)$_2$). In preferred embodiments, a prodrug of the invention comprises a substitution of a phenolic moiety or amine moiety of the active drug with a phosphate, phosphoramidate, or amino acid acyl group. A wide variety of methods for the preparation of prodrugs are known to those skilled in the art (see, for example, Pettit and Lippert, *Anti-Cancer Drug Design*, (2000), 15, 203-216).

Catechol prodrugs of the present invention are precursor forms of catechols that are metabolically converted in vivo to produce corresponding catechols. In a preferred implementation, the catechol prodrug of the invention comprises at least one phosphate replacing a hydroxyl moiety of the catechol. typically, the phosphate moiety has the general formula:

wherein each Y independently is OR or NHR, S$^-$, NH$^-$ or O$^-$, wherein each R independently is selected from hydrogen, $C_{1-6}$ alkyl, a mono or divalent metal cation, an ammonium cation; and Z is O or S.

"Hematopoietic neoplasm" refers to a cell proliferative disorder arising from cells of the hematopoietic lineage. Generally, hematopoiesis is the physiological process whereby undifferentiated cells or stem cells develop into various cells found in the peripheral blood. In the initial phase of development, hematopoietic stem cells, typically found in the bone marrow, undergo a series of cell divisions to form multipotent progenitor cells that commit to two main developmental pathways: the lymphoid lineage and the myeloid lineage. The committed progenitor cells of the myeloid lineage differentiate into three major sub-branches comprised of the erythroid, megakaryocyte, and granulocyte/monocyte developmental pathways. An additional pathway leads to formation of dendritic cells, which are involved in antigen presentation. The erythroid lineage gives rise to red blood cells while the megakaryocytic lineage gives rise to blood platelets. Committed cells of the granulocyte/monocyte lineage split into granulocyte or monocyte developmental pathways, the former pathway leading to formation of neutrophils, eosinophils, and basophils and the latter pathway giving rise to blood monocytes and macrophages.

Neoplasms of hematopoietic cells can involve cells of any phase of hematopoiesis, including hematopoietic stem cells, multipotent progenitor cells, oligopotent committed progenitor cells, precursor cells, and mature differentiated cells. The categories of hematopoietic neoplasms can generally follow the descriptions and diagnostic criteria employed by those of skill in the art (see, e.g., International Classification of Disease and Related Health Problems (ICD 10), World Health Organization (2003)). Hematopoietic neoplasms can also be characterized based on the molecular features, such as cell surface markers and gene expression profiles, cell phenotype exhibited by the aberrant cells, and/or chromosomal aberrations (e.g., deletions, translocations, insertions, etc.) characteristic of certain hematopoietic neoplasms, such as the Philadelphia chromosome found in chronic myelogenous leukemia. Other classifications include National Cancer Institute Working Formulation (Cancer, 1982, 49:2112-2135) and Revised European-American Lymphoma Classification (REAL).

The term "hematopoietic neoplasm" includes, but is not limited to, acute lymphoblastic leukemia (ALL), acute myelogenous leukemia (AML), chronic myelogenous leukemia (CML), chronic lymphocytic leukemia (CLL), hairy cell leukemia, Hodgkin's disease, non-Hodgkin's lymphoma, multiple myeloma, and myeloplastic syndrome.

"Myeloid neoplasm" refers to proliferative disorder of cells of the myeloid lineage of hematopoiesis. Neoplasms can arise from hematopoietic stem cells, myeloid committed progenitor cells, precursor cells, and terminally differentiated cells. Myeloid neoplasms can be subdivided based on the phenotypic attributes of the aberrant cells or the differentiated state from which the abnormal cells arise. Subdivisions include, among others, myeloproliferative diseases, myelodysplastic/myeloproliferative diseases, myelodysplastic syndromes, acute myeloid leukemia, and acute biphenotypic leukemia.

"Lymphoid neoplasm" refers a proliferative disorder involving cells of the lymphoid lineage of hematopoiesis. Lymphoid neoplasms can arise from hematopoietic stem cells as well as lymphoid committed progenitor cells, precursor cells, and terminally differentiated cells. These neoplasms can be subdivided based on the phenotypic attributes of the aberrant cells or the differentiated state from which the abnormal cells arise. Subdivisions include, among others, B cell neoplasms, T cell neoplasms, NK cell neoplasms, and Hodgkin's lymphoma. Committed progenitor cells of the lymphoid lineage develop into the B cell pathway, T cell pathway, or the non-T/B cell pathway. Similar to the myeloid lineage, an additional lymphoid pathway appears to give rise to dendritic cells involved in antigen presentation. The B cell progenitor cell develops into a precursor B cell (pre-B), which differentiates into B cells responsible for producing immunoglobulins. Progenitor cells of the T cell lineage differentiate into precursor T cells (pre-T) that, based on the influence of certain cytokines, develop into cytotoxic or helper/suppressor T cells involved in cell mediated immunity. Non-T/B cell pathway leads to generation of natural killer (NK) cells.

The term "hematopoietic neoplasm" includes, but is not limited to, acute lymphoblastic leukemia (ALL), acute myelogenous leukemia (AML), chronic myelogenous leukemia (CML), chronic lymphocytic leukemia (CLL), hairy cell leukemia, Hodgkin's disease, non-Hodgkin's lymphoma, multiple myeloma, and myeloplastic syndrome.

As used herein, the term "pharmaceutically acceptable salt" includes salts that are physiologically tolerated by a subject. Such salts are typically prepared from an inorganic and/or organic acid. Examples of suitable inorganic acids include, but are not limited to, hydrochloric, hydrobromic, hydroiodic, nitric, sulfuric, and phosphoric acid. Organic acids may be aliphatic, aromatic, carboxylic, and/or sulfonic acids. Suitable organic acids include, but are not limited to, formic, acetic, propionic, succinic, camphorsulfonic, citric, fumaric, gluconic, lactic, malic, mucic, tartaric, para-toluenesulfonic, glycolic, glucuronic, maleic, furoic, glutamic, benzoic, anthranilic, salicylic, phenylacetic, mandelic, pamoic, methanesulfonic, ethanesulfonic, pantothenic, benzenesulfonic (besylate), stearic, sulfanilic, alginic, galacturonic, and the like. Other pharmaceutically acceptable salts include alkali metal cations such as Na, K, Li; alkali earth metal salts such as Mg or Ca; or organic amine salts such as those disclosed in PCT International Application Nos. WO02/22626 or WO00/48606 and U.S. Pat. Nos. 6,855,702 and 6,670,344, which are incorporated herein by reference in their entireties. Particularly preferred salts include organic amine salts such tromethamine (TRIS) and amino acid salts such as histidine. Other exemplary salts that can be synthesized using the methods of the invention include those described in U.S. Pat. No. 7,018,987, which is incorporated by reference herein.

B. Methods of Treating Hematopoietic Neoplasms

Adhesion of leukemic cells to vascular cells may confer resistance to chemotherapeutic agents. Therefore, disruption of leukemic cell cytoskeletal stability and interference with vascular cell interactions should promote leukemic cell death. Indeed, as disclosed in greater detail below, low and non-toxic doses of the catechol compound combretastatin A-1 diphosphate (CA1dP) inhibit leukemic cell proliferation in vitro and induce mitotic arrest and cell death. In addition, CA1 dP rapidly increases intracellular reactive oxygen species (ROS), and antioxidant treatment provides partial protection from cell death. As such, combretastatin compounds comprising a catechol or quinone moiety, such as CA1dP, provide for an effective means to treat refractory organ-infiltrating leukemias.

Accordingly, one aspect of the present invention provides a method of treating a hematopoietic neoplasm, the method comprising administering, to a mammal suffering from a hematopoietic neoplasm, a therapeutically effective amount of a combretastatin compound comprising a catechol or quinone moiety. Preferably the combretastatin compound is combretastatin A1, a combretastatin A-1 prodrug (such as combretastatin A-1 diphosphate), or a pharmaceutically acceptable salt thereof.

Derived from the South African tree *Combreturn caffrum*, combretastatins such as combretastatin A-4 (CA-4) were initially identified in the 1980's as a potent inhibitors of tubulin polymerization. CA-4, and other combretastatins (e.g. CA-1) have been shown to bind at or near the colchicine binding site on tubulin with high affinity. In vitro studies clearly demonstrated that combretastatins are potent cytotoxic agents against a diverse spectrum of tumor cell types in culture. CA4P and CA1P, respective phosphate prodrugs of CA-4 and CA-1, were subsequently developed to combat problems with aqueous insolubility. Surprisingly, CA1P has also been shown to cause a rapid and acute shutdown of the blood flow to tumor tissue that is separate and distinct from the antiproliferative effects of the agents on tumor cells themselves. A number of studies have shown that combretastatins cause extensive shut-down of blood flow within the tumor microvasculature, leading to secondary tumor cell death (Dark et al., *Cancer Res.*, 57: 1829-34, (1997); Chaplin et al., *Anticancer Res.*, 19: 189-96, (1999); Hill et al., *Anticancer Res.*, 22(3):1453-8 (2002); Holwell et al., *Anticancer Res.*, 22(2A):707-11, (2002). Blood flow to normal tissues is generally far less affected by CA1P than blood flow to tumors, although blood flow to some organs, such as spleen, skin, skeletal muscle and brain, can be transiently inhibited.

As used herein, the term "combretastatin" or "combretastatin compound" denotes at least one of the combretastatin family of compounds, derivatives or analogs thereof, their prodrugs (preferably phosphate prodrugs) and derivatives thereof, and salts of these compounds. Combretastatins include those anti-cancer compounds isolated from the South African tree *Combreturn caffrum*, including without limitation, Combretastatins A-1, A-2, A-3, A-4, B-1, B-2, B-3, B-4, D-1, and D-2, and various prodrugs thereof, exemplified by Combretastatin A-4 phosphate (CA4P) compounds, Combretastatin A-1 diphosphate (CA1dP) compounds and salts thereof (see for example Pettit et al, *Can. J. Chem.*, (1982); Pettit et al., *J. Org. Chem.*, 1985; Pettit et al., *J. Nat. Prod.*, 1987; Lin et al., *Biochemistry*, (1989); Pettit et al., *J. Med. Chem.*, 1995; Pettit et al., *Anticancer Drug Design*, (2000); Pettit et al., *Anticancer Drug Design*, 16(4-5): 185-93 (2001)).

Combretastatin and combretastatin salts contemplated for use in the methods of the invention are described in WO 99/35150; WO 01/81355; WO 02/022626; U.S. Pat. Nos. 4,996,237; 5,409,953; 5,561,122; 5,569,786; 6,538,038; 6,670,344; 6,855,702; 7,018,987; 7,078,552; and 7,279,466. Derivatives or analogs of combretastatins also are described in Singh et al., *J. Org. Chem.*, 1989; Cushman et al, *J. Med. Chem.*, 1991; Getahun et al, *J. Med. Chem.*, 1992; Andres et al, *Bioorg. Med. Chem. Lett.*, 1993; Mannila, et al., *Liebigs. Ann. Chem.*, 1993; Shirai et al., *Bioorg. Med. Chem. Lett.*, 1994; Medarde et al., *Bioorg. Med. Chem. Lett.*, 1995; Wood et al, *Br. J. Cancer*, 1995; Bedford et al., *Bioorg. Med. Chem. Lett.*, 1996; Dorr et al., *Invest. New Drugs*, 1996; Jonnalagadda et al., *Bioorg. Med. Chem. Lett.*, 1996; Shirai et al., *Heterocycles*, 1997; Aleksandrzak, et al., *Anticancer Drugs*, 1998; Chen et al., *Biochem. Pharmacol.*, 1998; Ducki et al., *Bioorg. Med. Chem. Lett.*, 1998; Hatanaka et al., *Bioorg. Med. Chem. Lett.*, 1998; Medarde et al., *Eur. J. Med. Chem.*, 1998; Medina et al., *Bioorg. Med. Chem. Lett.*, 1998; Ohsumi et al., *Bioorg. Med. Chem. Lett.*, 1998; Ohsumi et al., *J. Med. Chem.*, 1998; Pettit, et al., *J. Med. Chem.*, 1998; Shirai et al., *Bioorg. Med. Chem. Lett.*, 1998; Banwell et al., *Aust. J. Chem.*, 1999; Medarde et al., *Bioorg. Med. Chem. Lett.*, 1999; Shan et al., *PNAS*, 1999; Combeau et al., *Mol. Pharmacol.*, 2000; Pettit et al., *J. Med. Chem.*, 2000; Pinney et al., *Bioorg. Med. Chem. Lett.*, 2000; Flynn et al., *Bioorg. Med. Chem. Lett.*, 2001; Gwaltney et al., *Bioorg. Med. Chem. Lett.*, 2001; Lawrence et al., 2001; Nguyen-Hai et al., *Bioorg. Med. Chem. Lett.*, 2001; Xia et al., *J. Med. Chem.*, 2001; Tahir et al., *Cancer Res.*, 2001; Wu-Wong et al., *Cancer Res.*, 2001; Janik et al, *Biooorg. Med. Chem. Lett.*, 2002; Kim et al., *Bioorg Med Chem. Lett.*, 2002; Li et al., *Biooorg. Med. Chem. Lett.*, 2002; Nam et al., *Bioorg. Med. Chem. Lett.*, 2002; Wang et al., *J. Med. Chem.* 2002; Hsieh et al., *Biooorg. Med. Chem. Lett.*, 2003; Hadimani et al., *Bioorg. Med. Chem. Lett.*, 2003; Mu et al., *J. Med. Chem.*, 2003; Nam et al., *Curr. Med. Chem.*, 2003; Pettit et al, *J. Med. Chem.*, 2003; Gaukroger et al., Org Biomol Chem. 2003; Bailly et al., J Med. Chem. 2003; Sun et al., Anticancer Res. 2004; Sun et al., Bioorg Med Chem. Lett. 2004; Liou et al., J Med. Chem. 2004; Perez-Melero et al., Bioorg Med Chem. Lett. 2004; Liou et al., J Med. Chem. 2004; Mamane et al., Chemistry. 2004; De Martini et al, J Med. Chem. 2004; Ducki et al, J Med. Chem. 2005; Maya et al., J Med. Chem. 2005; Medarde et al., J Enzyme Inhib Med. Chem. 2004; Simoni et al, J Med. Chem. 2005; Sanchez et al., Bioorg Med. Chem. 2005; Vongvanich et al., Planta Med. 2005; Tron et al., J Med. Chem. 2005; Borrel et al., Bioorg Med. Chem. 2005; Hsieh et al., Curr Pharm Des. 2005; Lawrence et al, Curr Pharm Des. 2005; Hadfield et al., Eur J Med. Chem. 2005; Pettit et al., J Med Chem. 2005; Coggioloa et al., Bioorg Med Chem. Lett. 2005; Kaffy et al., Org Biomol Chem. 2005; Mateo et al, J Org. Chem. 2005; LeBlanc et al., Bioorg Med. Chem. 2005; Srivistava et al., Bioorg Med. Chem. 2005; Nguyen et al., J Med. Chem. 2005; Kong et al., Chem. Biol. 2005; Li et al, Bioorg Med Chem. Lett. 2005; Pettit et al, J Nat. Prod. 2005; Nicholson et al, Anticancer Drugs. 2006; Monk et al., Bioorg. Med. Chem. 2006; De Martino et al., J Med. Chem. 2006; Peifer et al., J Med. Chem. 2006; Kaffy et al., Bioorg. Med. Chem. 2006; Banwell et al., Bioorg Med. Chem. 2006; Dupeyre et al., Bioorg Med. Chem. 2006 Simoni et al, J Med. Chem. 2006; Tron et al., J Med. Chem. 2006; Romagnoli et al, J Med. Chem. 2006; Pandit et al., Bioorg Med. Chem. 2006; Nakamura et al., ChemMedChem. 2006; Pirali et al., J Med. Chem. 2006; Bellina et al., Bioorg Med Chem. Lett. 2006; Hu et al, J Med. Chem. 2006; Chang et al., J Med. Chem. 2006; Thomson et al., Mol Cancer Ther. 2006; Fortin et al., Bioorg Med Chem. Lett., 2007; Duan et al., J Med. Chem., 2007; Zhang et al., J Med. Chem. 2007; Wu et al., Bioorg Med Chem. Lett. 2007; Sun et al., Bioorg Med Chem. Lett. 2007, WO 06/138427; WO 036743; WO 05/007635, WO 03/040077, WO 03/035008, WO 02/50007, WO 02/14329; WO 01/12579, WO 01/09103, WO 01/81288, WO 01/84929, WO 00/48590, WO 00/73264, WO 00/06556, WO 00/35865, WO 99/34788, WO 99/48495, WO 92/16486, U.S. Pat. Nos. 7,125,906; 7,105,695; 7,105,501; 7,087,627; 7,030,123; 7,078,552; 7,030,123; 7,018,987; 6,992,106; 6,919,324; 6,846,192, 6,855,702; 6,849,656; 6,794,384; 6,787,672, 6,777,578, 6,723,858, 6,720,323, 6,433,012, 6,423,753, 6,201,001, 6,150,407, 6,169,104, 5,731,353, 5,674,906, 5,430,062, 5,525,632, 4,996,237 and 4,940,726. Any combretastatin compound having a catechol or quinone moiety is suitable for use in the methods of the present invention.

In a preferred implementation, the combretastatin comprises a quinone or catechol, preferable an orthoquinone or ortho-catechol. Oxidation of an ortho-catechol, such as CA1, to an ortho-quinone can result in oxidative damage to neoplastic cells via redox cycling. This is a process in which the quinone is reduced to a radical (ie. semiquinone), which in turn reduces oxygen to superoxide radicals with the quinone being reformed or cycled. The generation of a quinone derivative from CA1 has been demonstrated in vivo and the quinone was found to react rapidly with the reducing agents glutathione and ascorbate. In addition, rapid consumption of oxygen in the presence of ascorbate confirmed the formation of CA1 quinone. Furthermore, redox-cycling, confirming the formation of CA1 semiquinone, was observed with CA1.

In a particular embodiment, the combretastatin compound is of the Formula I:

or a pharmaceutically acceptable salt thereof, wherein each $R^1$ independently is selected from $C_{1-6}$ alkoxy, halogen and halo-substituted $C_{1-6}$ alkyl;

each $R^2$ independently is selected from $C_{1-6}$ alkoxy, halogen and halo-substituted $C_{1-6}$ alkyl;

p is 1, 2, 3, or 4;

q is 0, 1 or 2;

$R^3$ and $R^4$ each independently is selected from hydroxyl or wherein each Y independently is $OR^5$ or $NHR^5$, or $O^-$, wherein each $R^5$ independently is selected from hydrogen and $C_{1-6}$ alkyl;

Z is O or S.

In a preferred implementation, the compound is a pharmaceutically acceptable salt of the compound of Formula I, wherein each of $R^3$ and $R^4$ is a phosphate:

wherein the cation of the salt can be either a divalent cation or two monovalent cations. Preferably, the divalent cation is a divalent metal cation. In some implementations, the monovalent cation is an alkali metal, an aliphatic amine or an ammonium. In other implementations, the monovalent cation is selected from the group consisting of sodium, TRIS, histidine, ethanolamine, diethanolamine, ethylenediamine, diethylamine, triethanolamine, glucamine, N-methylglucamine, ethylenediamine, 2-(4-imidazolyl)-ethylamine, choline, and hydrabamine.

In another embodiment, Formula I is represented by a compound of Formula II:

wherein
each $R^1$ independently is selected from $C_{1-6}$ alkoxy, halogen and halo-substituted $C_{1-6}$ alkyl;
$R^2$ is selected from $C_{1-6}$ alkoxy, halogen and halo-substituted $C_{1-6}$ alkyl;
$R^3$ and $R^4$ each independently is selected from hydroxyl or wherein
each Y independently is $OR^5$ or $NHR^5$, or $O^-$, wherein each $R^5$ independently is selected from hydrogen and $C_{1-6}$ alkyl;
Z is O or S.

In a particularly preferred implementation, the compound is combretastatin A-1 diphosphate (CA1 dP):

CA1dP or a pharmaceutically acceptable salt thereof.

The method of the invention can further comprise co-administering a chemotherapeutic agent, such a cytosine arabinoside (Ara-C), to the subject. "Co-administration" or "co-administering" can be in the form of a single formulation (combining, for example, CA1dP and Ara-C with pharmaceutically acceptable excipients, optionally segregating the two active ingredients in different excipient mixtures designed to independently control their respective release rates and durations) or by independent administration of separate formulations containing the active agents. "Co-administration" further includes concurrent administration (e.g. administration of CA1 dP and a Ara-C at the same time) and time varied administration (administration of CA1 dP at a time different from that of the Ara-C), as long as both the combretastatin A-1 diphosphate, or a pharmaceutically acceptable salt thereof, and the chemotherapeutic agent, e.g., Ara-C, are present in the body in therapeutically effective concentrations during at least partially overlapping times. In preferred implementations the chemotherapeutic agent is Ara-C, etoposide, thioguanine or cyclophosphamide.

A "chemotherapeutic agent" is a chemical compound useful in the treatment of cancer. Examples of chemotherapeutic agents include alkylating agents such as thiotepa and CYTOXAN® (cyclophosphamide); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma11 and calicheamicin omega11 (see, e.g., Agnew, Chem. Intl. Ed. Engl., 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®) and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UF-TORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine (Ara-C), dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., paclitaxel (TAXOL®), albumin-engineered nanoparticle formulation of paclitaxel (ABRAXANE™), and doxetaxel (TAXOTERE®); chloranbucil; 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

As is well-known in the art, solid tumors are quite distinct from non-solid tumors, such as those found in hematopoietic-related cancers. Examples of non-solid tumors include leukemias, such as myeloid leukemias and lymphoid leukemias, myelomas, and lymphomas. In some implementations, the non-solid tumor is a hematopoietic neoplasm, which is aberrant growth of cells of the hematopoietic system. Hematopoietic malignancies can have their origins in pluripotent stem cells, multipotent progenitor cells, oligopotent committed progenitor cells, precursor cells, and terminally differentiated cells involved in hematopoiesis. Some hematological malignancies are believed to arise from hematopoietic stem cells, which have the ability for self renewal. For instance, cells capable of developing specific subtypes of acute myeloid leukemia (AML) upon transplantation display the cell surface markers of hematopoietic stem cells, implicating hematopoietic stem cells as the source of leukemic cells. Although hematopoietic neoplasms often originate from stem cells, committed progenitor cells or more terminally differentiated cells of a developmental lineage can also be the source of some leukemias. For example, forced expression of the fusion protein Bcr/Abl (associated with chronic myelogenous leukemia) in common myeloid progenitor or granulocyte/macrophage progenitor cells produces a leukemic-like condition.

Hematopoietic neoplasms differ from solid tumors in being capable of circulating and having access to various organs through interaction with activated vascular cells. Indeed, some hematopoietic neoplastic cells may adhere to vascular cells, establishing perivascular infiltrates, and as such may be endowed with a unique mechanism of resistance to chemotherapy. Both circulating and vascular-adherent hematopoietic neoplasms require cytoskeletal stability to maintain mitochondrial and cellular function and avoid cell death. Low and non-toxic doses of combretastatins and combretastatin compounds comprising a catechol or quinone moiety, can selectively induce apoptosis of circulating and vascular-bound leukemic cells, leading to cell death. This induction of apoptosis occurs by a caspase-dependent mechanism as well as ROS-mediated mitochondrial damage. Thus, combretastatin compounds comprising a catechol or quinone moiety are effective in treating hematopoietic neoplasms, as demonstrated by their ability to target hematopoietic neoplasms in vitro and in vivo and to eradicate circulating, marrow- and organ-resident vascular-adherent hematopoietic neoplasms.

In some implementations, the hematopoietic neoplasm treated is a lymphoid neoplasm, where the abnormal cells are derived from and/or display the characteristic phenotype of cells of the lymphoid lineage. Lymphoid neoplasms can be subdivided into B-cell neoplasms, T and NK-cell neoplasms, and Hodgkin's lymphoma. B-cell neoplasms can be further subdivided into precursor B-cell neoplasm and mature/peripheral B-cell neoplasm. Exemplary B-cell neoplasms are precursor B-lymphoblastic leukemia/lymphoma (precursor B-cell acute lymphoblastic leukemia) while exemplary mature/peripheral B-cell neoplasms are B-cell chronic lymphocytic leukemia/small lymphocytic lymphoma, B-cell prolymphocytic leukemia, lymphoplasmacytic lymphoma, splenic marginal zone B-cell lymphoma, hairy cell leukemia, plasma cell myeloma/plasmacytoma, extranodal marginal zone B-cell lymphoma of MALT type, nodal marginal zone B-cell lymphoma, follicular lymphoma, mantle-cell lymphoma, diffuse large B-cell lymphoma, mediastinal large B-cell lymphoma, primary effusion lymphoma, and Burkitt's lymphoma/Burkitt cell leukemia. T-cell and NK-cell neoplasms are further subdivided into precursor T-cell neoplasm and mature (peripheral) T-cell neoplasms. Exemplary precursor T-cell neoplasm is precursor T-lymphoblastic lymphoma/leukemia (precursor T-cell acute lymphoblastic leukemia) while exemplary mature (peripheral) T-cell neoplasms are T-cell prolymphocytic leukemia T-cell granular lymphocytic leukemia, aggressive NK-cell leukemia, adult T-cell lymphoma/leukemia (HTLV-1), extranodal NK/T-cell lymphoma, nasal type, enteropathy-type T-cell lymphoma, hepatosplenic gamma-delta T-cell lymphoma, subcutaneous panniculitis-like T-cell lymphoma, Mycosis fungoides/Sezary syndrome, Anaplastic large-cell lymphoma, T/null cell, primary cutaneous type, Peripheral T-cell lymphoma, not otherwise characterized, Angioimmunoblastic T-cell lymphoma, Anaplastic large-cell lymphoma, T/null cell, primary systemic type. The third member of lymphoid neoplasms is Hodgkin's lymphoma, also referred to as Hodgkin's disease. Exemplary diagnosis of this class that can be treated with the compounds include, among others, nodular lymphocyte-predominant Hodgkin's lymphoma, and various classical forms of Hodgkin's disease, exemplary members of which are Nodular sclerosis Hodgkin's lymphoma (grades 1 and 2), Lymphocyte-rich classical Hodgkin's lymphoma, Mixed cellularity Hodgkin's lymphoma, and Lymphocyte depletion Hodgkin's lymphoma. In various implementations, any of the lymphoid neoplasms can be treated with the combretastatin compounds of the invention.

In some implementations, the hematopoietic neoplasm treated is a myeloid neoplasm. This group comprises a large class of cell proliferative disorders involving or displaying the characteristic phenotype of the cells of the myeloid lineage. Myeloid neoplasms can be subdivided into myeloproliferative diseases, myelodysplastic/myeloproliferative diseases, myelodysplastic syndromes, and acute myeloid leukemias.

Exemplary myeloproliferative diseases are chronic myelogenous leukemia (e.g., Philadelphia chromosome positive (t(9; 22)(qq34; q11)), chronic neutrophilic leukemia, chronic eosinophilic leukemia/hypereosinophilic syndrome, chronic idiopathic myelofibrosis, polycythemia vera, and essential thrombocythemia. Exemplary myelodysplastic/myeloproliferative diseases are chronic myelomonocytic leukemia, atypical chronic myelogenous leukemia, and juvenile myelomonocytic leukemia. Exemplary myelodysplastic syndromes are refractory anemia, with ringed sideroblasts and without ringed sideroblasts, refractory cytopenia (myelodysplastic syndrome) with multilineage dysplasia, refractory anemia (myelodysplastic syndrome) with excess blasts, 5q-syndrome, and myelodysplastic syndrome. In various implementations, any of the myeloid neoplasms can be treated with the combretastatin compounds of the invention.

In some implementations, combretastatin compounds comprising a quinone or catechol, can be used to treat acute myeloid leukemias (AML), which represent a large class of myeloid neoplasms having its own subdivision of disorders. These subdivisions include, among others, AMLs with recurrent cytogenetic translocations, AML with multilineage dysplasia, and other AML not otherwise categorized. Exemplary AMLs with recurrent cytogenetic translocations include, among others, AML with t(8; 21)(q22; q22), AML1(CBF-alpha)/ETO, Acute promyelocytic leukemia (AML with t(15; 17)(q22; q11-12) and variants, PML/RAR-alpha), AML with abnormal bone marrow eosinophils (inv(16)(p13q22) or t(16; 16)(p13; q11), CBFb/MYH11X), and AML with 11q23 (MLL) abnormalities. Exemplary AML with multilineage dysplasia are those that are associated with or without prior myelodysplastic syndrome. Other acute myeloid leukemias not classified within any definable group include, AML minimally differentiated, AML without maturation, AML with maturation, acute myelomonocytic leukemia, acute monocytic leukemia, acute erythroid leukemia, acute megakaryocytic leukemia, acute basophilic leukemia, and acute panmyelosis with myelofibrosis.

One aspect of the invention is a pharmaceutical composition useful for treating a hematopoietic neoplasm in a mammal, which composition comprises combretastatin compound comprising a quinone or catechol, in combination with a pharmaceutically acceptable excipient. The composition is prepared in accordance with known formulation techniques to provide a composition suitable for oral, topical, transdermal, rectal, by inhalation, parenteral (intravenous, intramuscular, or intraperitoneal) administration, and the like. Detailed guidance for preparing compositions of the invention are found by reference to the $18^{th}$ or $19^{th}$ Edition of Remington's Pharmaceutical. Sciences, Published by the Mack Publishing Co., Easton, Pa. 18040. In certain implementations, the pharmaceutical composition further comprises a chemotherapeutic agent, such as Ara-C, etoposide, thioguanine or cyclophosphamide.

Unit doses or multiple dose forms are contemplated, each offering advantages in certain clinical settings. The unit dose would contain a predetermined quantity of active compound calculated to produce the desired effect(s) in the setting of treating cancer. The multiple dose form may be particularly useful when multiples of single doses, or fractional doses, are required to achieve the desired ends. Either of these dosing forms may have specifications that are dictated by or directly dependent upon the unique characteristic of the particular compound, the particular therapeutic effect to be achieved, and any limitations inherent in the art of preparing the particular compound for treatment of cancer.

A unit dose will contain a therapeutically effective amount sufficient to treat a hematopoietic neoplasm in a subject and may contain from about 1.0 to 1000 mg of compound, for example about 50 to 500 mg.

The combretastatin compound comprising a catechol or quinone moiety preferably is administered parenterally, e.g., intravenously, intramuscularly, intravenously, subcutaneously, or intraperitoneally. The carrier or excipient or excipient mixture can be a solvent or a dispersive medium containing, for example, various polar or non-polar solvents, suitable mixtures thereof, or oils. As used herein "carrier" or "excipient" means a pharmaceutically acceptable carrier or excipient and includes any and all solvents, dispersive agents or media, coating(s), antimicrobial agents, iso/hypo/hypertonic agents, absorption-modifying agents, and the like. The use of such substances and the agents for pharmaceutically active substances is well known in the art. Except insofar as any conventional media or agent is incompatible with the active ingredient, use in therapeutic compositions is contemplated. Moreover, other or supplementary active ingredients can also be incorporated into the final composition.

Solutions of the compound may be prepared in suitable diluents such as water, ethanol, glycerol, liquid polyethylene glycol(s), various oils, and/or mixtures thereof, and others known to those skilled in the art.

The pharmaceutical forms suitable for injectable use include sterile solutions, dispersions, emulsions, and sterile powders. The final form must be stable under conditions of manufacture and storage. Furthermore, the final pharmaceutical form must be protected against contamination and must, therefore, be able to inhibit the growth of microorganisms such as bacteria or fungi. A single intravenous or intraperitoneal dose can be administered. Alternatively, a slow long term infusion or multiple short term daily infusions may be utilized, typically lasting from 1 to 8 days. Alternate day or dosing once every several days may also be utilized.

Sterile, injectable solutions are prepared by incorporating a compound in the required amount into one or more appropriate solvents to which other ingredients, listed above or known to those skilled in the art, may be added as required. Sterile injectable solutions are prepared by incorporating the compound in the required amount in the appropriate solvent with various other ingredients as required. Sterilizing procedures, such as filtration, then follow. Typically, dispersions are made by incorporating the compound into a sterile vehicle which also contains the dispersion medium and the required other ingredients as indicated above. In the case of a sterile powder, the preferred methods include vacuum drying or freeze drying to which any required ingredients are added.

In all cases the final form, as noted, must be sterile and must also be able to pass readily through an injection device such as a hollow needle. The proper viscosity may be achieved and maintained by the proper choice of solvents or excipients. Moreover, the use of molecular or particulate coatings such as lecithin, the proper selection of particle size in dispersions, or the use of materials with surfactant properties may be utilized.

Prevention or inhibition of growth of microorganisms may be achieved through the addition of one or more antimicrobial agents such as chlorobutanol, ascorbic acid, parabens, thimerosal, or the like. It may also be preferable to include agents that alter the tonicity such as sugars or salts.

The combretastatin compound comprising a catechol or quinone moiety also can be administered orally in a suitable formulation as an ingestible tablet, a buccal tablet, capsule, caplet, elixir, suspension, syrup, trouche, wafer, lozenge, and the like. Generally, the most straightforward formulation is a tablet or capsule (individually or collectively designated as an "oral dosage unit"). Suitable formulations are prepared in accordance with a standard formulating techniques available that match the characteristics of the compound to the excipients available for formulating an appropriate composition. A tablet or capsule will preferably contain about 50 to about 500 mg of such a combretastatin compound.

The form may deliver a compound rapidly or may be a sustained-release preparation. The compound may be enclosed in a hard or soft capsule, may be compressed into tablets, or may be incorporated with beverages, food or otherwise into the diet. The percentage of the final composition and the preparations may, of course, be varied and may conveniently range between 1 and 90% of the weight of the final form, e.g., tablet. The amount in such therapeutically useful compositions is such that a suitable dosage will be obtained. Preferred compositions according to the current invention are prepared so that an oral dosage unit form contains between about 5.0 to about 50% by weight (% w) in dosage units weighing between 5 and 1000 mg.

The suitable formulation of an oral dosage unit may also contain: a binder, such as gum tragacanth, acacia, corn starch, gelatin; sweetening agents such as lactose or sucrose; disintegrating agents such as corn starch, alginic acid and the like; a lubricant such as magnesium stearate; or flavoring such a peppermint, oil of wintergreen or the like. Various other materials may be present as coating or to otherwise modify the physical form of the oral dosage unit. The oral dosage unit may be coated with shellac, a sugar or both. Syrup or elixir may contain the compound, sucrose as a sweetening agent, methyl and propylparabens as a preservative, a dye and flavoring. Any material utilized should be pharmaceutically-acceptable and substantially non-toxic. Details of the types of excipients useful may be found in the nineteenth edition of "Remington: The Science and Practice of Pharmacy," Mack Printing Company, Easton, Pa. See particularly chapters 91-93 for a fuller discussion.

Another aspect of this invention is a method for treating a hematopoietic neoplasm in a warm-blooded animal, which method comprises administering a therapeutically effective amount of a combretastatin compounds comprising a catechol or quinone moiety. A combretastatin compound useful in this invention is administered to an appropriate subject in need of these agents in a therapeutically effective dose by a medically acceptable route of administration such as orally, parentally (e.g., intramuscularly, intravenously, subcutaneously, interperitoneally), transdermally, rectally, by inhalation and the like.

With mammals, including humans, the effective amounts can be administered on the basis of body surface area. The interrelationship of dosages varies for animals of various sizes and species, and for humans (based on mg/m$^2$ of body surface) is described by E. J. Freireich et al., Cancer Chemother. Rep., 50(4):219 (1966). Body surface area may be approximately determined from the height and weight of an individual (see, e.g., Scientific Tables, Geigy Pharmaceuticals, Ardsley, N.Y. pp. 537-538 (1970)). A suitable dose range is from 1 to 1000 mg of equivalent per m$^2$ body surface area of a compound of the invention, for instance from 50 to 500 mg/m$^2$.

Another important feature of the method provided by the present invention relates to the relatively low apparent overall toxicity of the derivatives administered in accordance with the teachings herein. Overall toxicity can be judged using various criteria. For example, loss of body weight in a subject over 10% of the initially recorded body weight (i.e., before treatment) can be considered as one sign of toxicity. In addition, loss of overall mobility and activity and signs of diarrhea or cystitis in a subject can also be interpreted as evidence of toxicity.

VI. EXAMPLES

A. Example 1

Subcutaneous In Vivo Leukemia Model

HL60 (1×10$^7$ cells in 0.1 ml) were injected subcutaneously into the dorsa of 4-6 week old athymic nu/nu mice (Southern Research Institute). When palpable tumors were evident (average tumor volume 100 mm$^3$; i.e. approximately 12 days after inoculation), 6 experimental groups of mice were randomized, each with 10 animals. Treatment was initiated according to the following regimens:

| Group | Animals | Compound | Dose | Treatment Schedule |
|---|---|---|---|---|
| 1 | 10 | Control (PBS) | 0 | Q4D × 2/2 wks (SD) – Q3H × 3 ( ) |
| 2 | 10 | CA1dP | 75 mg/kg/inj | Q7D × 2 (SD + 1) |
| 3 | 10 | CA4P | 75 mg/kg/inj | Q7D × 2 (SD + 1) |
| 4 | 10 | Ara-C | 20 mg/kg/inj | Q4D × 2/2 wks (SD) – Q3H × 3 ( ) |
| 5 | 10 | CA1dP | 75 mg/kg/inj | Q7D × 2 (SD + 1) |
|   |    | Ara-C | 20 mg/kg/inj | Q4D × 2/2 wks (SD) – Q3H × 3 ( ) |
| 6 | 10 | CA4P | 75 mg/kg/inj | Q7D × 2 (SD + 1) |
|   |    | Ara-C | 20 mg/kg/inj | Q4D × 2/2 wks (SD) – Q3H × 3 ( ) |

Figure 1:
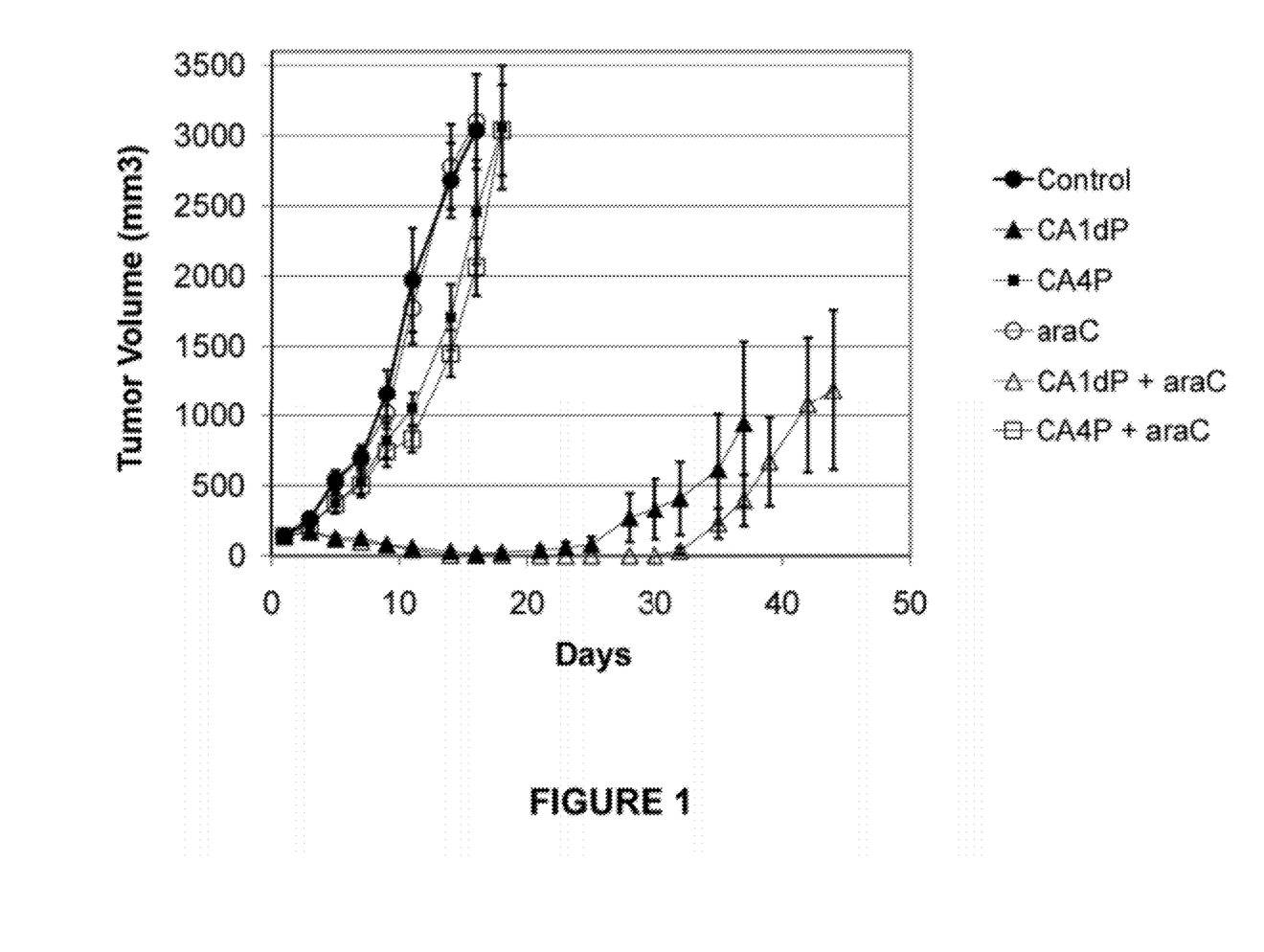
FIG. 1 illustrates average tumor volume (±SD) as a function of time for subcutaneous HL60 tumors treated with CA4P, CA1dP and/or AraC.
Figure 2:
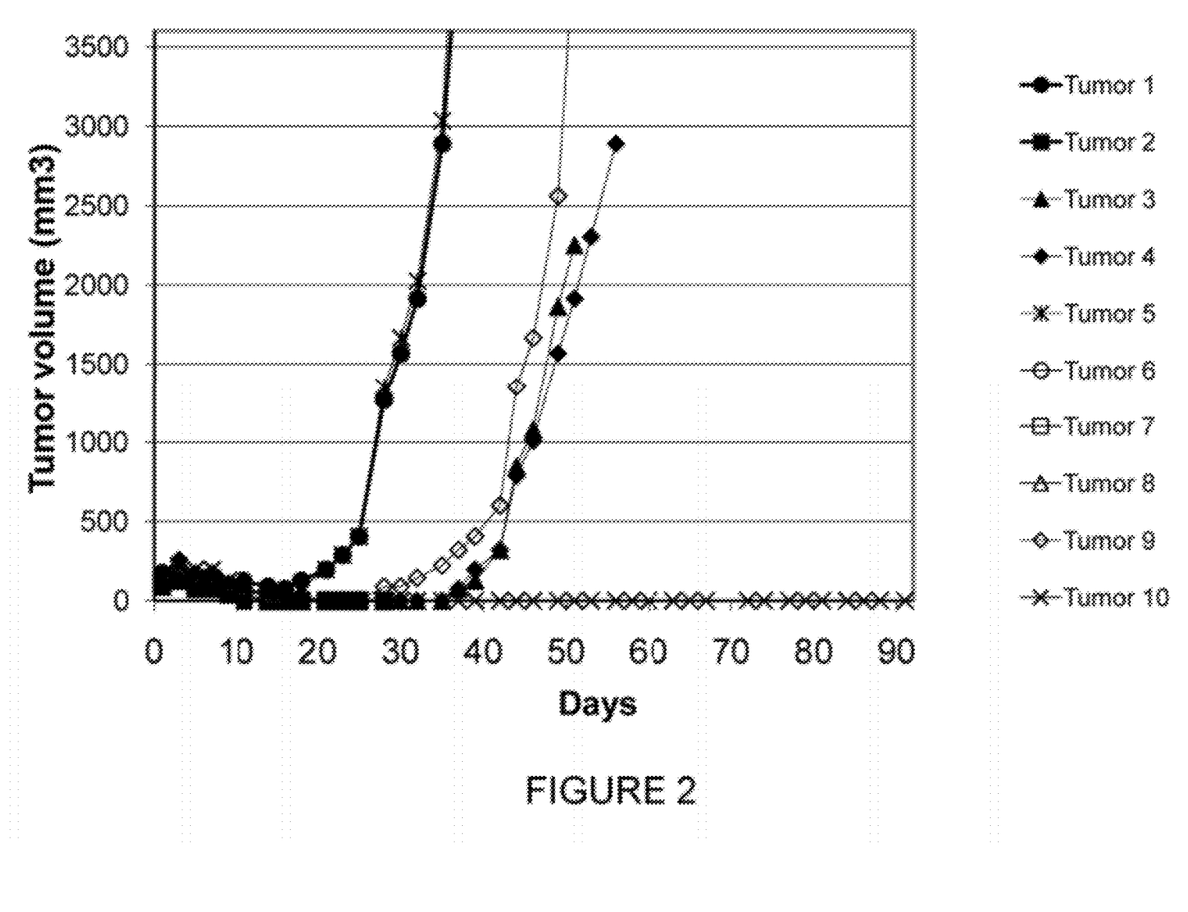
FIGS. 2 and 3 provide individual tumor volumes for selected experiments summarized in FIG. 1.
Figure 3:
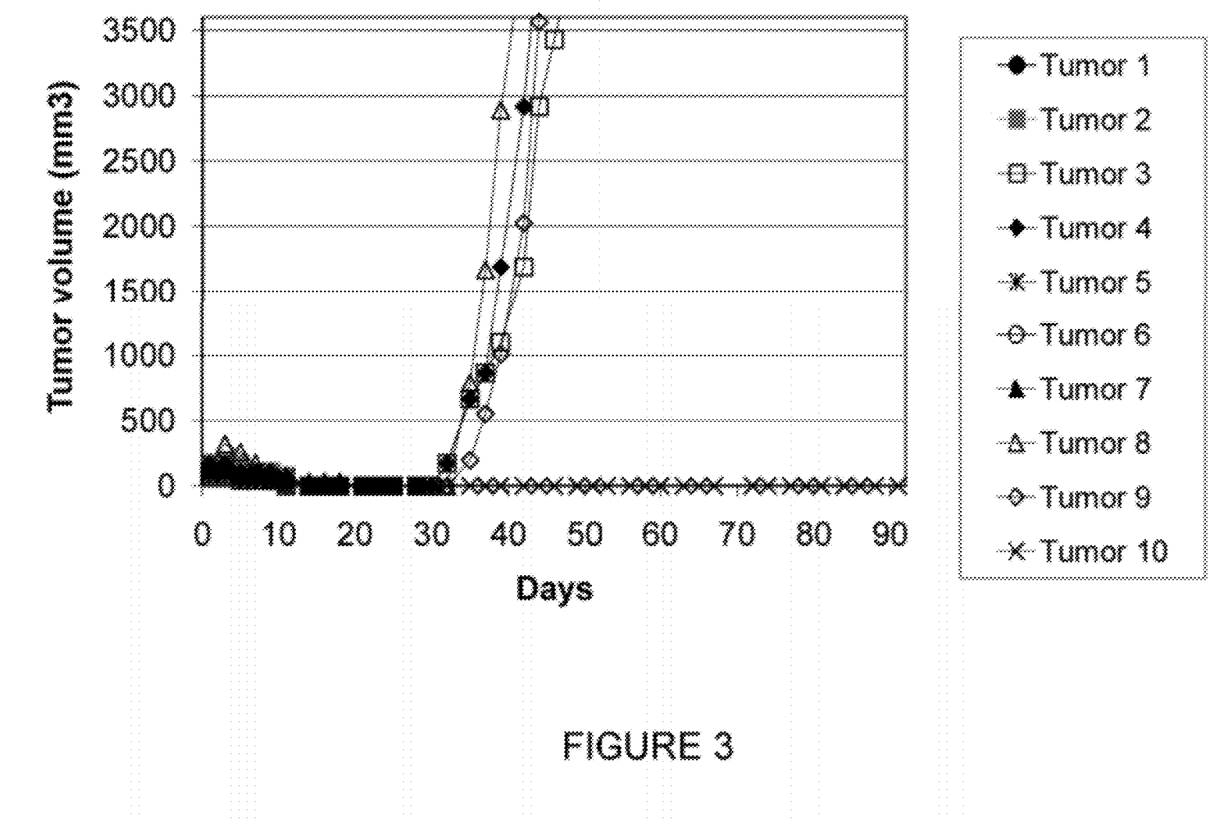

Tumor volume was measured three times a week until the endpoint was reached (tumor volume >3000 mm$^3$), or for 90 days post-treatment. Treatment with Ara-C alone showed little improvement over treatment with phosphate buffered saline (control). Treatment with CA4P as a single agent showed delayed tumor growth and extended life span as compared to controls (See FIG. 1). Treatment with an ortho-quinone prodrug, CA1dP, demonstrated substantial decreases in tumor volume and five complete tumor regressions in a population of ten treated mice (FIG. 2). Addition of Ara-C to CA1dP further decreased tumor volumes and led to six complete regressions out of ten treated mice (FIG. 3).

A. Example 2

Dose Response Activity

HL60 (1×10$^7$ cells in 0.1 ml) were injected subcutaneously into the dorsa of 4-6 week old athymic nu/nu mice (Southern Research Institute). When palpable tumors were evident (average tumor volume 100 mm$^3$; i.e. approximately 12 days after inoculation), ten experimental groups of mice were randomized, each with 10 animals. Treatment was initiated according to the following regimens:

| Group | Compound | Dose | Treatment Schedule |
|---|---|---|---|
| 1 | Control | 0 mg/kg/inj |  |
| 2 | CA1dP | 75 mg/kg/inj | day 3 and 10 |
| 3 | CA1dP | 25 mg/kg/inj | day 3 and 10 |
| 4 | CA1dP | 10 mg/kg/inj | day 3 and 10 |
| 5 | CA1dP | 2.5 mg/kg/inj | day 3 and 10 |
| 6 | Ara-C | 20 mg/kg/inj | tid day 1, 4, 8 and 12 |
| 7 | Ara-C + CA1dP | 20 mg/kg/inj<br>75 mg/kg/inj | tid day 1, 4, 8 and 12<br>day 3 and 10 |

-continued

| Group | Compound | Dose | Treatment Schedule |
|---|---|---|---|
| 8 | Ara-C + CA1dP | 20 mg/kg/inj | tid day 1, 4, 8 and 12 |
|   |   | 25 mg/kg/inj | day 3 and 10 |
| 9 | Ara-C + CA1dP | 20 mg/kg/inj | tid day 1, 4, 8 and 12 |
|   |   | 10 mg/kg/inj | day 3 and 10 |
| 10 | Ara-C + CA1dP | 20 mg/kg/inj | tid day 1, 4, 8 and 12 |
|   |   | 2.5 mg/kg/inj | day 3 and 10 |

Figure 4:
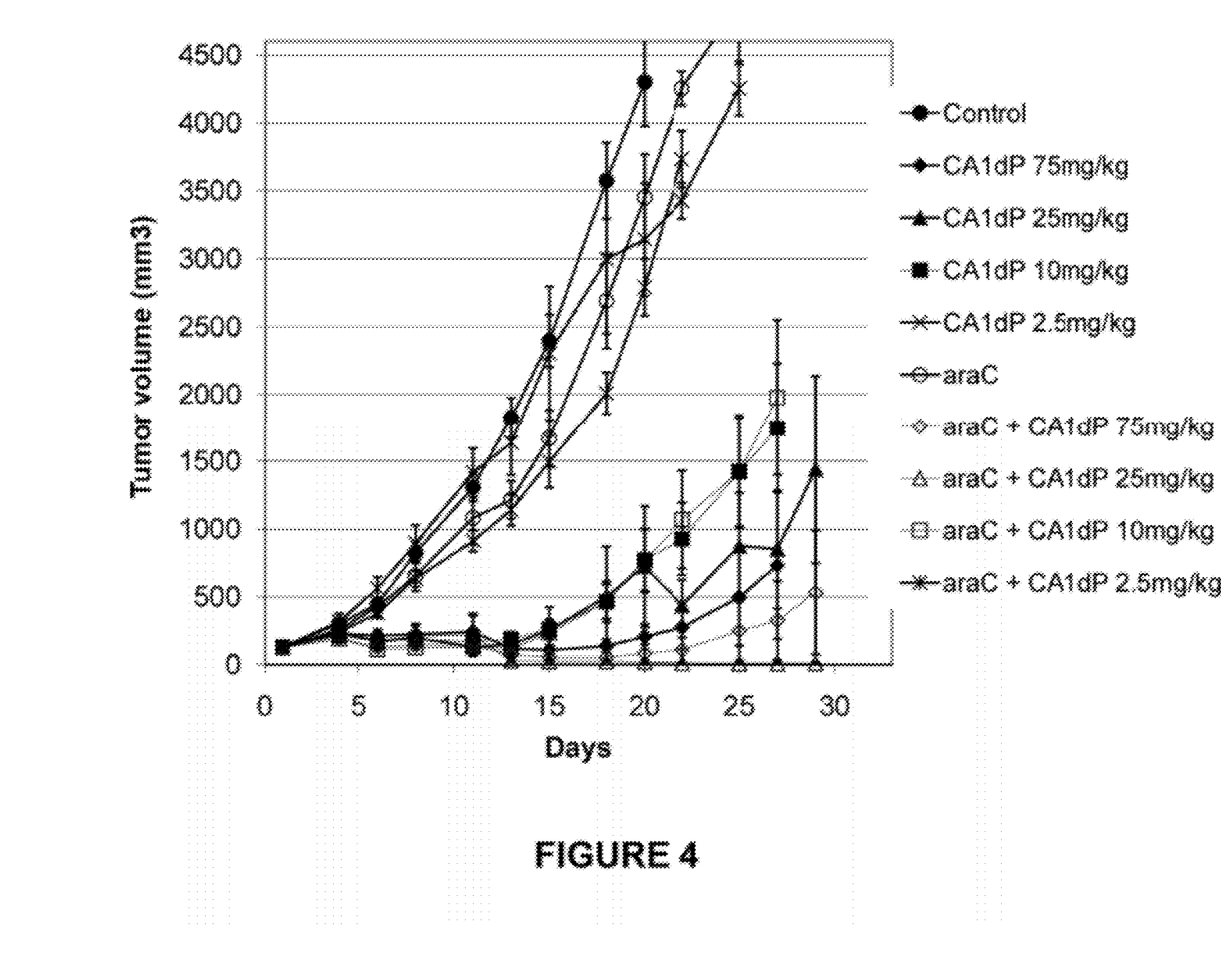
FIG. 4 illustrates the dose response activity of CA1dP (±AraC) against leukemia cells.

Tumor volume was measured three times per week. The decrease in tumor volume showed a clear dose response relationship relative to the dose of CA1dP administered (See FIG. 4). administration of doses of CA1dP above 2.5 mg/kg showed significant anti-tumor activity. Wlthough the number of complete responses was not significantly altered by the combination with araC, tumors showed longer growth inhibition following treatment with CA1 dP and araC as compared to tumors treated with CA1dP alone.

Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

We claim:

1. A method of treating a myeloid neoplasm comprising administering a therapeutically effective amount of a combretastatin compound, or a pharmaceutically acceptable salt thereof, to a subject having a hematological malignancy, wherein the combretastatin compound is combretastatin A-1 diphosphate (CA1dP):

CA1dP or a pharmaceutically acceptable salt thereof.

2. The method of claim 1, wherein the combretastatin compound is a pharmaceutically acceptable salt of combretastatin A-1 diphosphate (CA1dP),-wherein the cation of the salt can be either a divalent cation or two monovalent cations.

3. The method of claim 2, wherein, the divalent cation is a divalent metal cation.

4. The method of claim 2, wherein, the monovalent cation is an alkali metal, an aliphatic amine or an ammonium.

5. The method of claim 2, wherein, the monovalent cation is selected from the group consisting of sodium, TRIS, histidine, ethanolamine, diethanolamine, ethylenediamine, diethylamine, triethanolamine, glucamine, N-methylglucamine, ethylenediamine, 2-(4-imidazolyl)-ethylamine, choline, and hydrabamine.

6. The method of claim 1, wherein the myeloid neoplasm is an acute myeloid leukemia (AML).

7. The method of claim 1, wherein the myeloid neoplasm is a refractory organ-infiltrating leukemia.

8. The method of claim 1, wherein the pharmaceutically acceptable salt is a potassium salt of combretastatin A-1 diphosphate.

9. The method of claim 1, further comprising co-administering a chemotherapeutic agent to the subject having a myeloid neoplasm.

10. The method of claim 9, wherein the chemotherapeutic agent is Ara-C, etoposide, thioguanine or cyclophosphamide.

11. The method of claim 3, wherein the divalent metal cation is magnesium or calcium.

* * * * *